United States Patent [19]

Valorose et al.

[11] Patent Number: 5,215,754
[45] Date of Patent: Jun. 1, 1993

[54] SWALLOWABLE TABLET CONTAINING POLYCARBOPHIL

[75] Inventors: Joseph J. Valorose, Orange, N.Y.; Bala V. Iyer, Overland Park, Kans.

[73] Assignee: American Cyanamid Company, Stamford, Conn.

[21] Appl. No.: 338,840

[22] Filed: Apr. 14, 1989

Related U.S. Application Data

[63] Continuation of Ser. No. 947,653, Dec. 30, 1986, abandoned.

[51] Int. Cl.$^5$ .............................. A61K 9/28
[52] U.S. Cl. .................. 424/474; 424/78.18; 424/78.26; 424/78.37; 514/867
[58] Field of Search ............ 514/960, 974, 867; 424/80, 474, 78.16, 78.26, 78.37

[56] References Cited

U.S. PATENT DOCUMENTS

| | | | |
|---|---|---|---|
| 4,029,815 | 6/1977 | Sherlock et al. | 514/535 |
| 4,666,703 | 5/1987 | Kopf | 514/960 |
| 4,684,534 | 8/1987 | Valentive | 424/447 |
| 4,753,801 | 6/1988 | Oren et al. | 424/465 |

Primary Examiner—Thurman K. Page
Assistant Examiner—P. Kulkosky
Attorney, Agent, or Firm—Alan M. Gordon

[57] ABSTRACT

A novel dosage form of calcium polycarbophil, useful in the treatment of bowel dysfunction, is described.

8 Claims, No Drawings

SWALLOWABLE TABLET CONTAINING POLYCARBOPHIL

This is a continuation of application Ser. No. 947,653, filed Dec. 30, 1986 now abandoned.

This invention is concerned with bowel dysfunction, specifically bulking agents for use in the treatment of constipation and diarrhea. This invention more particularly pertains to new dosage forms of calcium polycarbophil, a recognized bulking agent.

Calcium polycarbophil is the calcium salt of polyacrylic acid cross-linked with divinyl glycol, and may be represented by the following structure:

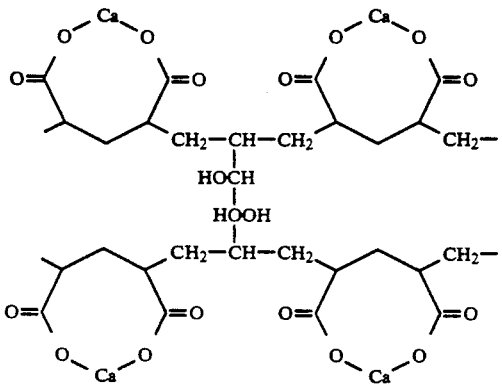

The acid is at least about 82% neutralized with calcium and the salt must not contain more than about 10% water. Pharmaceutical grade calcium polycarbophil will absorb about 35 or more times its weight in water. Its use in the treatment of diarrhea and constipation is described in U.S. Pat. No. 3,297,664 and elsewhere in the literature.

Commercial use of calcium polycarbophil for diarrhea and constipation has been restricted to chewable wafers. For example, A. H. Robins Company of Richmond, Va., markets chewable tablets containing calcium polycarbophil as active ingredient under the trademark MITROLAN ® for bowel dysfunction. Such wafers contain ingredients other than calcium polycarbophil, including, inter alia, sugar, flavorings, artificial colors, etc. Despite such added ingredients, the wafers are unpleasant to ingest.

The present invention provides means for making calcium polycarbophil into a more efficient, effective and new dosage form. The advantages of this composition of matter over other bulk laxatives such as METAMUCIL ® (psyllium); CITROCEL ® (hydroxypropylmethylcellulose); and MITROLAN ® (calcium polycarbophil in the form of a chewable tablet) are:

1. Site specific; swelling occurs in the intestines (the desired site) and not immediately in the stomach as other bulk laxatives do. This eliminates potential gas and bloating problems.
2. On a weight for weight basis, the composition of the present invention absorbs four times more water than psyllium and hydroxypropylmethylcellulose, providing improved intestinal motility.
3. Convenience in administration; the composition of the present invention may be administered as one or more tablets once or twice daily versus one to three teaspoons of powder dissolved in liquid one to three times daily, or two wafers chewed and ingested four times daily.
4. Patient compliance is improved with a tablet versus either a reconstitutable powder or a chewable wafer.
5. Optimum tablet dosage form, easy slip-swallow coating versus MITROLAN ® chewable tablet which has an unpleasant taste and a gritty, chalky texture.
6. Does not contain sugar, sodium, starch, lactose or artificial colorants and contains less than one calorie.

The bulk laxative tablets of the present invention may be formulated in the following ranges:

| Ingredient | mg/Tablet |
| --- | --- |
| Calcium polycarbophil U.S.P. | 312.5-937.5* |
| Microcrystalline cellulose N.F. | 100-250 |
| Magnesium stearate N.F. | 2-11 |
| Crospovidone N.F.** | 25-75 |
| Caramel powder*** | 8-20 |
| Povidone U.S.P.**** | 15-50 |
| Silica gel N.F. | 3-10 |
| Stearic acid N.F. | 5-30 |

*Supplies 250-750 mg of polycarbophil
**Crospovidone is cross-linked polyvinylpyrrolidone N.F. grade.
***Caramel powder consists of natural caramel color such as Caramel R.T. No. 175 ®, a product of Sethness Products Co., 2667 West Logan Blvd., Chicago, IL 60647.
****Povidone is polyvinylpyrrolidone U.S.P. grade.

The size of the tablet is controlled by compression weight and tooling size.

Specifically it is most desirable to manufacture the tablet of the present invention according to the following formula:

| | |
| --- | --- |
| Calcium polycarbophil U.S.P. | 625 mg* |
| Microcrystalline cellulose N.F. | 195 mg |
| Magnesium stearate N.F. | 5.5 mg |
| Crospovidone N.F. | 50 mg |
| Caramel color R.T. No. 175 ® | 13 mg |
| Povidone U.S.P. | 25 mg |
| Silica gel N.F. | 5 mg |
| Stearic acid N.F. | 15 mg |

*Provides 500 mg of polycarbophil.

The tablets of the present invention can be made as follows. In a suitable granulator, such as an AMF or a Collette, calcium polycarbophil, caramel color, povidone and a small portion of the crospovidone are placed. The ingredients are then dry blended for about 15 minutes. Using purified water heated to about 50°-65° C., the blended powder is then granulated. The resulting wet mass is then milled, and dried. The dried granulation is then sifted, any oversize granulation being further milled and screened.

In another blender, the dried, milled and screened granules are placed, and silica gel, microcrystalline cellulose and the remaining crospovidone are added. The mixture is then blended for about 25 minutes or until a uniform blend has been achieved. The magnesium stearate and stearic acid are then added, or, preferably, approximately one-half of the blend is removed and such half mixed with the magnesium stearate and the stearic acid and then the resulting mixture is transferred back to the blender for further blending. In either case, the final mixture is blended until uniform.

The resulting material is then compressed into tablets and film-coated for ease in oral administration.

What is claimed is:

1. A swallowable tablet, designed to remain intact until it reaches the stomach, comprising: calcium polycarbophil as the sole active ingredient, microcrystalline cellulose, magnesium stearate, crospovidone as a disintegrant, providone, silica gel, stearic acid and a film coating to assist in swallowing said tablet.

2. The swallowable tablet as recited in claim 1 further comprising caramel powder.

3. The swallowable tablet as recited in claim 1 further comprising 312.5-937.5 mg of calcium polycarbophil; 100-250 mg microcrystalline cellulose; 2-11 mg magnesium stearate; 25-75 mg crospovidone; 15-50 mg povidone; 3-10 mg silica gel; and 5-30 mg stearic acid.

4. The swallowable tablet as recited in claim 3 further comprising 8-20 mg caramel color.

5. The swallowable tablet as recited in claim 3 further comprising: 625 mg calcium polycarbophil; 195 mg microcrystalline cellulose; 5.5 mg magnesium stearate; 50 mg crospovidone; 25 mg povidone; 5 mg silica gel; and 15 mg stearic acid.

6. The swallowable tablet as recited in claim 5 further comprising 13 mg caramel color.

7. A method for treating bowel dysfunction such as diarrhea and constipation in a warm-blooded animal which comprises administering a swallowable tablet as recited in claim 1.

8. A method for making a swallowable tablet containing calcium polycarbophil as the sole active ingredient, designed to remain intact until it reaches the stomach, which comprises:
(a) mixing calcium polycarbophil, crospovidone and povidone;
(b) granulating the mixture by adding 50°-65° C. water;
(c) milling the wet granulation;
(d) drying the milled granulation;
(e) further milling the dried granulation to achieve uniform granule size;
(f) blending crospovidone, silica and microcrystalline cellulose with the milled, dried granules;
(g) adding magnesium stearate and stearic acid to the blended mixture;
(h) compressing the resulting mixture into tablets; and
(i) coating the tablet with film to assist in swallowing said tablet.

* * * * *